United States Patent
Watson

(10) Patent No.: US 8,987,543 B1
(45) Date of Patent: Mar. 24, 2015

(54) SIZEABLE SANITARY OR INCONTINENCE PAD WITH MED ALERTS

(71) Applicant: Lillian A. Watson, Scappoose, OR (US)

(72) Inventor: Lillian A. Watson, Scappoose, OR (US)

(*) Notice: Subject to any disclaimer, the term of this patent is extended or adjusted under 35 U.S.C. 154(b) by 0 days.

(21) Appl. No.: 14/067,748

(22) Filed: Oct. 30, 2013

(51) Int. Cl.
- A61F 13/15 (2006.01)
- A61F 13/20 (2006.01)
- A61B 5/20 (2006.01)

(52) U.S. Cl.
CPC ................................. A61B 5/208 (2013.01)
USPC ............ 604/361; 604/375; 604/386; 604/390

(58) Field of Classification Search
CPC ......... A61F 13/20; A61F 13/15; A61F 13/02; A61B 5/00
USPC ............ 604/358, 387–402, 385.05, 361, 362, 604/367, 375, 317, 318, 322, 386; 600/584; 4/245.1; 2/400–406; 128/854, 855
See application file for complete search history.

(56) References Cited

U.S. PATENT DOCUMENTS

| | | | | |
|---|---|---|---|---|
| 5,468,236 A | * | 11/1995 | Everhart et al. | 604/361 |
| 6,114,595 A | * | 9/2000 | Moore et al. | 604/370 |
| 6,524,290 B2 | * | 2/2003 | Motta et al. | 604/385.01 |
| 2010/0100008 A1 | * | 4/2010 | Chciuk et al. | 600/584 |
| 2010/0221313 A1 | * | 9/2010 | Smith et al. | 424/448 |

* cited by examiner

Primary Examiner — Tatyana Zalukaeva
Assistant Examiner — Benedict L C Hanrahan
(74) Attorney, Agent, or Firm — Mark S. Hubert

(57) ABSTRACT

A sanitary or incontinence pad includes micro-perforated seams. On each side of the micro-perforated seam are sealed seams to retain the absorbent material within the pad. Tearing along the micro-perforated seam allows the pad to be separated into smaller functioning units to better meet the user's needs. Medical alert reagent tabs can be added to the surface of the pads to alert the user of possible health conditions.

1 Claim, 7 Drawing Sheets

SIZEABLE SANITARY OR INCONTINENCE PAD WITH MED ALERTS

BACKGROUND OF THE INVENTION

Both sanitary pads and incontinence pads serve the same purpose, to keep bodily fluids from spreading to a user's clothing. Users' requirements of these products can vary drastically. A man or woman that experiences minor bladder leakage when sneezing or laughing does not require the same level of protection from leakage as women during overnight menses. Accordingly, manufactures offer a large variety of products to accommodate a user's needs. For example, many manufactures of both sanitary pads and incontinence pads offer variations such as: liners, light, medium, heavy, overnight, with wings, and without wings. Medium, heavy, and overnight products are progressively larger in surface area and often thicker to capture more fluid. Users are often left buying a variety of products, and all of the products fail to account for body size. A 100-pound woman simply does not have the same physical configuration as a 250-pound woman. While the 100 pound woman might require the protection of the "heavy" product, the larger physical size of the "heavy" product would be clearly visible through her clothing, as her smaller frame simply cannot accommodate such a large sanitary or incontinence pad.

Urinalysis and blood work can disclose evidence of diseases, even some that have not caused significant signs or symptoms. Therefore, urinalysis and blood work are commonly part of routine health screening testing for pregnancy, urinary tract infections, high blood pressure, diabetes etc, as well as illegal substance screenings. Unfortunately, screenings at clinics and doctors' offices are both time consuming and expensive.

SUMMARY OF THE INVENTION

At the heart of the present invention is a sizable sanitary or incontinence pad for both women and men. The pad is seam-sealed on each side of a micro-perforated seam(s) as to lock-in the absorption material within the pad. The user can easily select the appropriate size or shape of the pad, based on his or her individual needs or physical requirements by simply tearing the pad along the micro-perforated seam(s). The remaining (unused) portion remains fully functionable for later use; each section is a functioning unit. Additionally, medical alert reagent tabs can be added to the surface of the pads to alert the user of possible health conditions without visiting a clinic or doctor's office. The pads are sealed in an airtight package to preserve the integrity of the medical alert tabs, and may additionally be housed in a separate resealable package.

DETAILED DESCRIPTION

Figure 1:
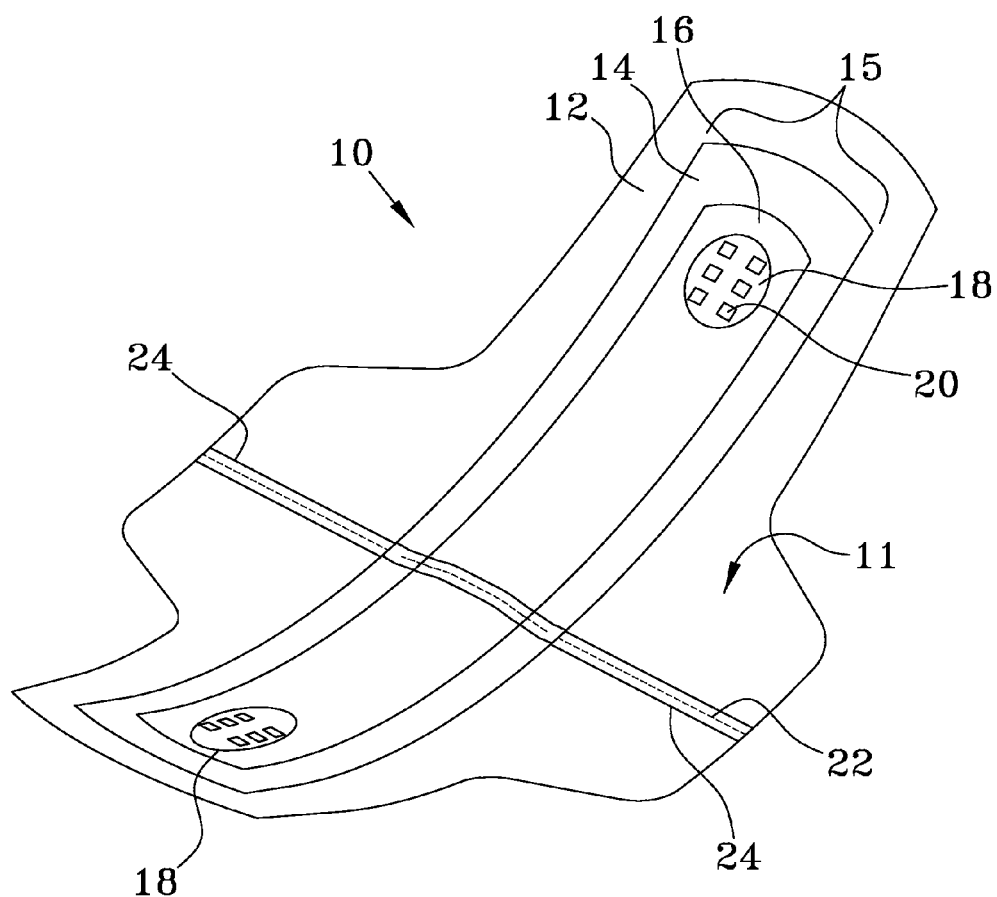
FIG. 1 is a perspective view of a first embodiment sanitary/incontinence pad embodying the invention.

As used herein, the term "sanitary pad," "incontinence pad," or "pad" refers to an absorbent device, which absorbs and contains body fluids, specifically menstrual blood and urine.

Looking at FIG. 1-5 a first embodiment sanitary/incontinence pad 10 comprising a first absorbent area 12, a second absorbent area 14, and third absorbent area 16 is illustrated. Pad 10 has two surfaces, a body-contacting surface 11 and a clothing surface 13, which is opposite body-contacting surface 11 (not illustrated in FIG. 1). Body-contacting surface 11 would be worn adjacent to the body of the user, while the clothing surface 13 is secured to the undergarment of the user. As is well known in the art, body-contacting surface 11 may be covered in a hydrophilic, liquid pervious top sheet (not illustrated) to aid in moving fluid away from the body of the user and into first, second, and third 12, 14, 16 absorbent areas. Although not illustrated A suitable top sheet may be manufactured from a wide range of materials, such as woven and nonwoven natural fibers, synthetic fibers, or from a combination of natural and synthetic fibers, and/or polymers. The user's body remains dry, creating a more comfortable wearing experience for the user. The top sheet is secured to the body-contacting surface 11 by any means that is well known in the art, such as heat bonds, pressure bonds, or an adhesive layer around the periphery of body-contacting surface 11.

Second and third absorbent areas 14, 16 form the absorbent core 15 of pad 10. As illustrated, third absorbent area 16 possesses a greater absorbent capacity than second absorbent area 14, and second absorbent area 14 has a greater absorbent capacity than first absorbent area 12. However, the absorbent capacity of first, second, and third, areas 12, 14, 16, may be varied without departing from the scope of the invention. Absorbent core 15 may be manufactured in a variety of sizes, shapes, and thicknesses, and from a variety of absorbent materials as is well known in the art. For example, absorbent core 15 may be rectangular, elliptical, hourglass, etc., in shape and may be profiled as to be thicker in the center, or at its ends. Absorbent core 15 may further be constructed from natural absorbent fibers such as natural organic absorbent fibers such as: creped cellulose, cotton, bamboo; synthetic absorbent fibers such as polyester, absorbent gelling materials, or absorbent polymers, etc., or any suitable combination.

Figure 3:
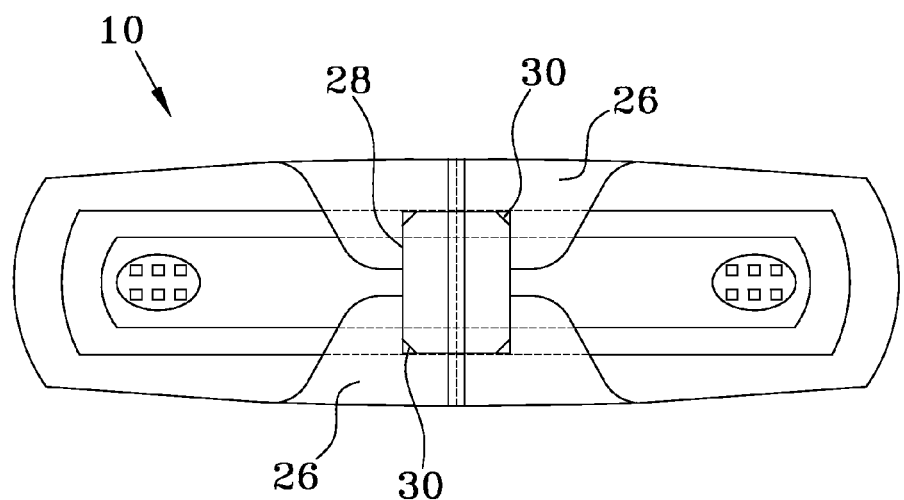
FIG. 3 is a top partial phantom view of a first embodiment sanitary/incontinence pad embodying the invention with the wings secured via a wing release liner.
Figure 5:
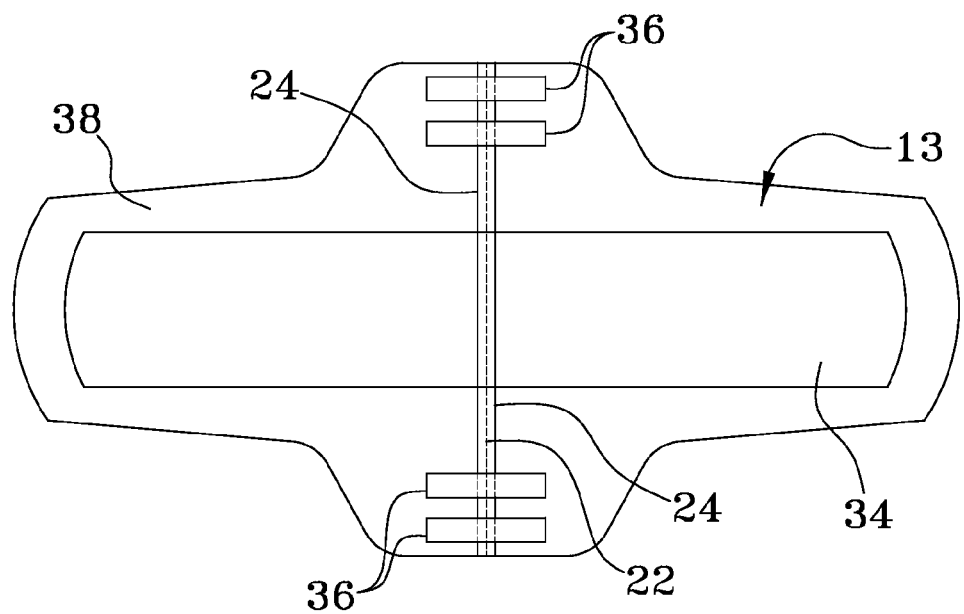
FIG. 5 is a bottom view of a first embodiment sanitary/incontinence pad embodying the invention illustrating the pressure sensitive adhesive means and wing-adhesive attachment means.

Two wings 26, each of which are adjacent to and extend laterally from the longitudinal edges of the first absorbent area 12, are configured to fold over the edges of the user's underwear so as to be disposed between the thighs of the user and the edges of the user's underwear. Wings 26 are provided with an wing-adhesive attachment means 36 to enable wings 26 to be secured to the garment facing side of the user's underwear as is well known in the art. As illustrated in FIG. 5, wing-adhesive attachment means 36 are two parallel rectangular regions of pressure sensitive adhesive. A removable wing-release liner 28 secures wings 26 together as illustrated in FIG. 3 in order to keep the adhesive from drying or adhering to an unintended surface prior to use. For ease of removal of the removable wing-release liner 28 from wing-adhesive attachment means 36 the removable wing-release liner 28 comprises dog-earned corner tabs 30 for easy grip and removal by the user.

Figure 4:
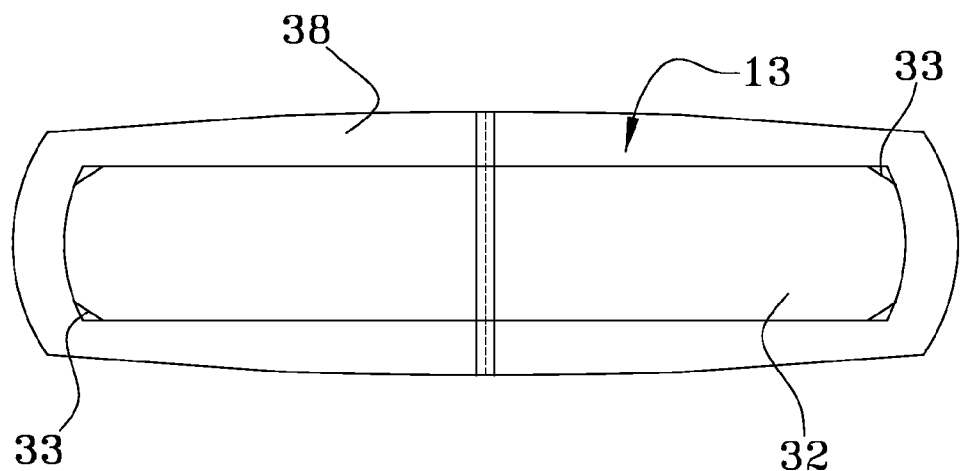
FIG. 4 is a bottom view of a first embodiment sanitary/incontinence pad embodying the invention with the wings secured via a wing release liner and the pressure sensitive adhesive means covered with a removeable release liner.

Looking at FIGS. 4-5, clothing surface 13 may comprise a backsheet 38, which is impervious to liquids and can be manufactured from any suitable hydrophobic material such as a plastic film. Backsheet 38 prevents bodily fluids contained in the absorbent core 15, or from first absorbent area 12 from soiling or wetting the garment to which pad 10 is secured. Backsheet 38 is joined to top sheet by attachment means (not shown) such as those well known in the art; for example, by a uniform continuous layer of adhesive, heat bonds, or pressure bonds. In embodiments where a top sheet is not employed, backsheet 38 is simply secured directly around the periphery of body-contacting surface 11. Pressure sensitive adhesive means 34 resides on backsheet 38 for releasable attachment with an article of clothing (underwear), and is covered with a removable release liner 32 in order to keep the adhesive from drying or adhering to an unintended surface prior to use. As illustrated in FIG. 5 pressure sensitive adhesive means 34 is a layer of pressure sensitive adhesive generally matching the shape of absorbent core 15. For ease of removal, the removable release line comprises dog-earned corner body tabs 33 for easy grip and removal by the user. In an alternate embodiment not employing a backsheet 38, a pressure sensitive adhesive means 34 may be applied directly to the clothing contacting surface 13.

Figure 2:
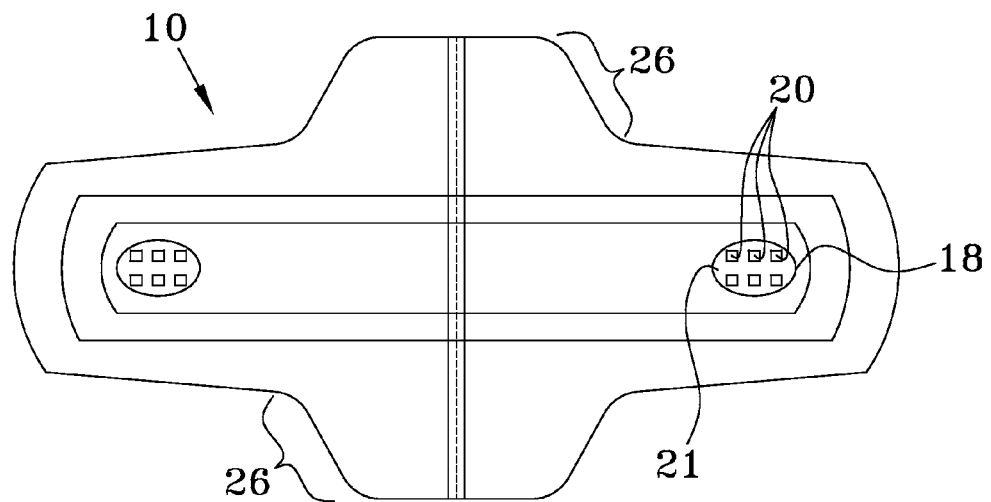
FIG. 2 is a top view of a first embodiment sanitary/incontinence pad embodying the invention.

Looking at FIG. 1-3 two reagent test tab areas 18 can be seen containing reagent test tabs 20. Individual tabs 20 may provide tests for glucose, bilirubin, ketone, specific gravity, blood, pH, protein, urobilinogen nitrite, nitrates, leukocytes, pregnancy, THC, etc. Reagent test tab areas 18 may be located on any region of the absorbent core 15 and may be comprised of a non-reactive substrate 21 with one or more reagent test tabs 20 secured to the non-reactive substrate 21 via any suitable adhesive. Non-reactive substrate 21 is secured to absorbent core 15 via any suitable adhesive. The addition of reagent test tab areas 18 to pad 10 is a convenient and effective way to alert the user of possible health conditions without the need for costly and time intensive clinic or doctor visits. In applications in which a top sheet is used, the non-reactive substrate 21 is secured directly to the top sheet. In another embodiment reagent test tab area 18 can be packaged separately for placement on pad 10 by the user. A pressure sensitive adhesive would be applied to the non-reactive substrate 21 and then covered with a release liner. Should a user desire to test for glucose levels in his urine, for example, he would simply remove the release line, secure the reactive substrate 21 (containing one or more tabs 20) to body-contacting surface 11 of pad 10, and secure pad 10 to his/her underwear. Additionally, tabs 20 can be grouped on a non-reactive substrate 21 to test for specific issues: e.g. drug use, kidney functioning, liver functioning, etc.

The reagent test tab area 18 is described as an "area" because the test tabs 20 may be embedded within absorbent core 15, within a top sheet, or anywhere along body-contacting surface 11, or for ease of manufacture the reagent test tab area 18 may secured to a backing or non-reactive substrate 21 which is then secured to a pad in any suitable manner, whether that be the manufacturer or by a user. Since the pads embodying the invention herein are customizable in geometric configuration, each user may have a preferred configuration as well as preferred placement in his/her clothing (underwear). Accordingly the best placement for the test tab area 18 may vary from user to user.

It can be seen in FIG. 1-5 that pad 10 is latterly bisected by micro-perforated seam 22. Micro-perforated seam 22 is comprised of micro-perforations that extend through the entire thickness of pad 10 allowing the user to separate the pad 10 along seam 22. To prevent any leakage of material from the first, second, and third absorbent areas 12, 14, 16, pad 10 has two seam seals 24, on each side of micro-perforated seam 22; thereby allowing the user to obtain two fully functional sanitary/incontinence pads without losing any of the absorbent material within, after pad 10 has been separated via tearing along micro-perforated seam 22. FIG. 3 illustrates that micro-perforated seam 22 extends through removable wing-release liner 28, which secures wings 26 together as well as the underlying wing-adhesive attachment means 36 (FIG. 5). Turning to FIG. 4-5, micro-perforated seam 22 extends through pressure sensitive adhesive means 34 and the removable release liner 32.

Figure 6:
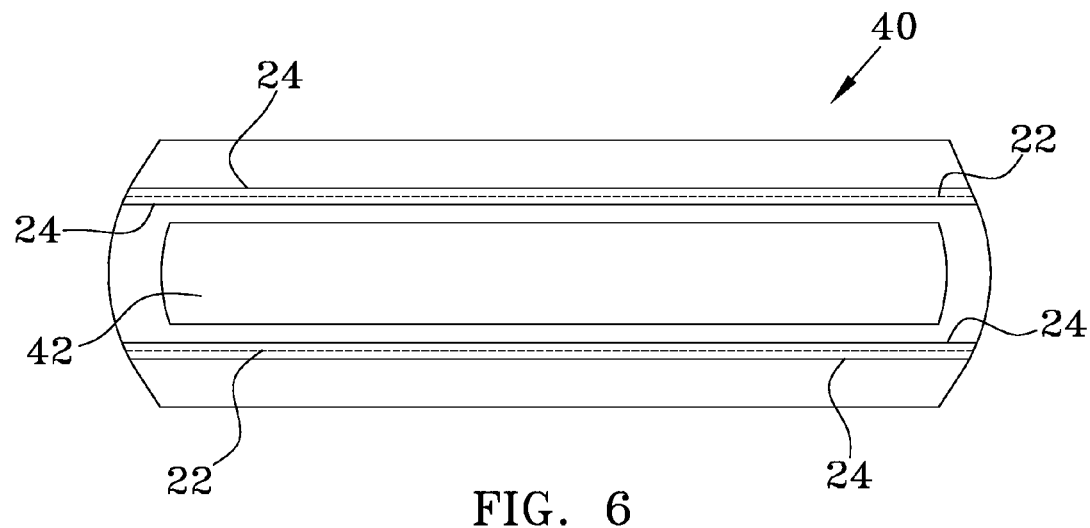
FIG. 6 is a top view of a second embodiment sanitary/incontinence pad embodying the invention.

Turning to FIG. 6 a top view of a second embodiment sanitary/incontinence pad 40 is illustrated. Second embodiment pad 40 has two micro-perforated seams 22 that run parallel the longitudinal axis of pad 40 adjacent the absorbent region 42. Again, each micro-perforated seam 22 has two seam seals 24, on each side of micro-perforated seam 22; thereby allowing the user to obtain two fully functional sanitary/incontinence pads without losing any of the absorbent material within, after pad 40 has been separated via tearing along either or both micro-perforated seams 22.

Figure 7:
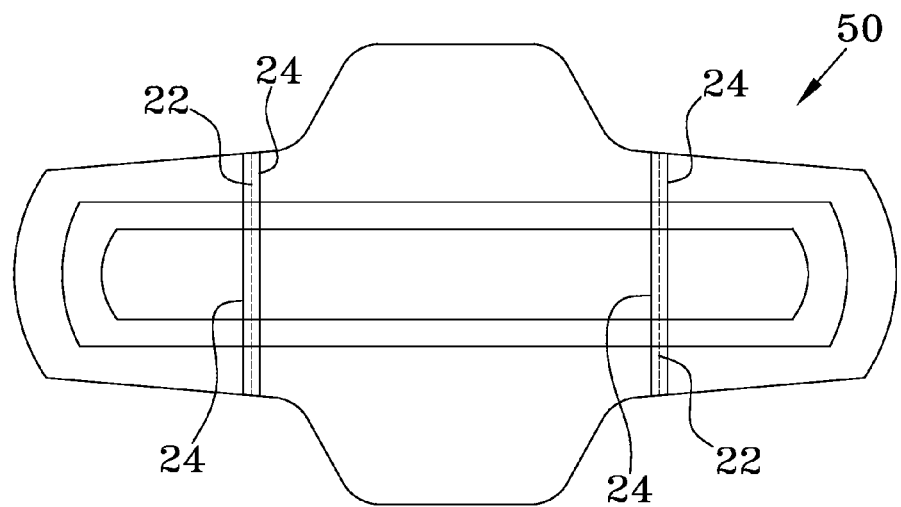
FIG. 7 is a top view of a third embodiment sanitary/incontinence pad embodying the invention.

Illustrated in FIG. 7 is a top view of the third embodiment sanitary/incontinence pad 50 of the present invention. Third embodiment pad 50 has been segmented, roughly in thirds, via two micro-perforated seams 22 parallel to pad 50's lateral axis, with seam seals 24 flanking each micro-perforated seam 22. A user can separate pad 50 into two or three fully functioning sanitary/incontinence pads per her/his own physical needs, and the unused portion can be simply saved for later use.

Figure 8:
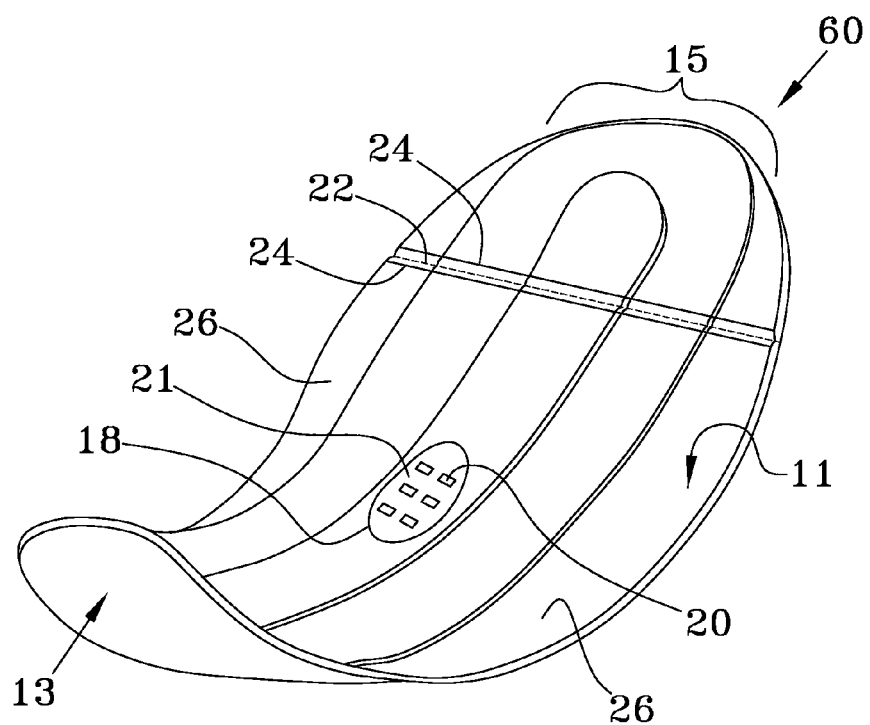
FIG. 8 is a perspective view of a fourth embodiment sanitary/incontinence pad embodying the invention.
Figure 9:
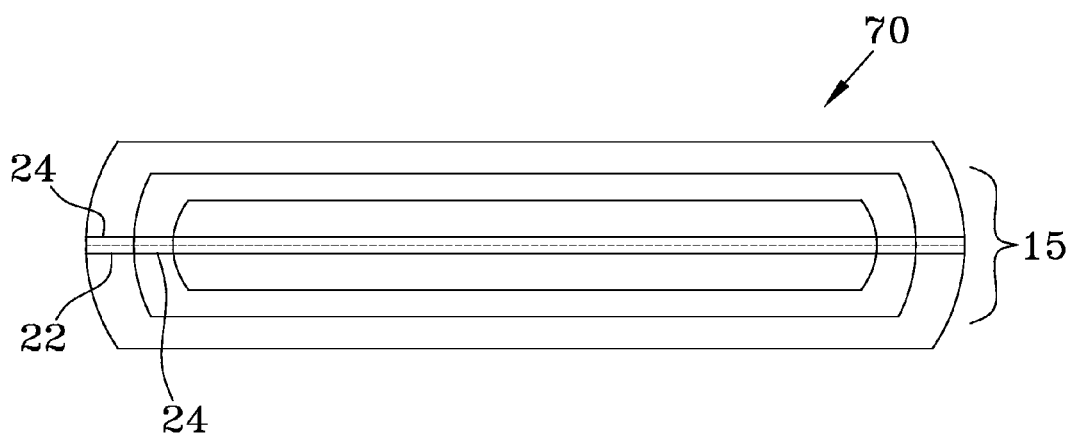
FIG. 9 is a top view of a fifth embodiment sanitary/incontinence pad embodying the invention.

Turning to FIGS. 8 & 9, fourth and fifth embodiment sanitary/incontinence pads 60 and 70 respectively are illustrated. Fifth embodiment sanitary/incontinence pad 70 illustrates an alternative arrangement for micro-perforated seam 22, wherein micro-perforated seam resides along the longitudinal axis of fifth embodiment pad 70. Fourth embodiment pad 60 illustrates a winged sanitary/incontinence pad similar in construction to first embodiment pad 10 (See FIG. 1-5), however, differing in shape. Generally, elliptical in shape fourth embodiment pad 60 has two wings 26 each of which are adjacent to and extend laterally from the longitudinal edges of absorbent core 15, and are configured to fold over the edges of the user's underwear. Micro-perforated seam 22 resides laterally along the upper third of pad 60. Again, the micro-perforated seam 22 has two seam seals 24, on each side of micro-perforated seam 22; thereby allowing the user to obtain two fully functional sanitary/incontinence pads without losing any of the absorbent material within, after pad 40 has been separated via tearing along micro-perforated seam 22. Additionally, fourth embodiment pad 60 contains a single reagent test tab areas 18 located on the absorbent core 15 and is comprised of a non-reactive substrate 21 with one or more reagent test tabs 20 secured to the non-reactive substrate 21 via any suitable adhesive.

Figure 10:
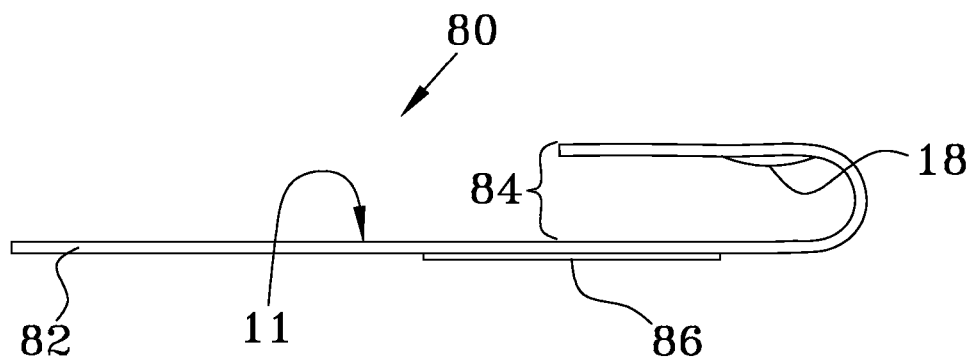
FIG. 10 is a side view of a sixth embodiment sanitary/incontinence pad embodying the invention.
Figure 11:
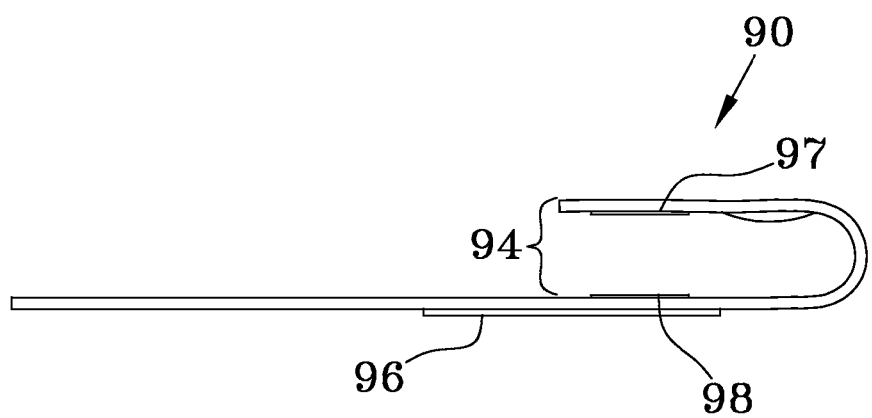
FIG. 11 is a side view of a seventh embodiment sanitary/incontinence pad embodying the invention.
Figure 12:
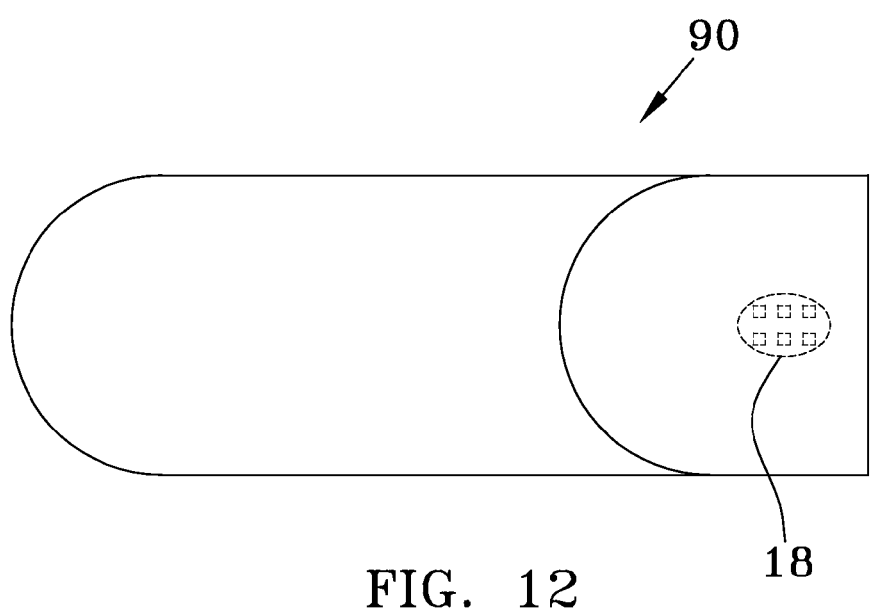
FIG. 12 is a top partial phantom view of a seventh embodiment sanitary/incontinence pad embodying the invention.

Finally, while the first through fifth embodiments discussed above are directed to both men and women, the sixth and seventh embodiments illustrated in FIGS. 10-12 are directed towards men. Turning to FIG. 10 a side view of seventh embodiment incontinence pad 80 is illustrated. Ultra absorbent pad body 82 is designed to cradle the glans penis within pocket 84. Adhesive tab 86 can be used to secure pad 80 to the users underwear. Pad 80 may also comprise a reagent test tab area 18. As illustrated in seventh embodiment 90 (FIGS. 11 & 12), to further aid in enclosing the glans penis within pocket 94, upper adhesive strip 97 and lower adhesive strip 98 residing along the peripheral edge can facilitate securing pocket 94 around the penis. Once the glans penis has been inserted in pocket 94, the user would simply secure upper strip 97 to lower strip 98, rendering embodiments 80 and 90 size-adjustable per the user's needs/requirements. Additionally, the user is not restricted to securing upper strip 97 only to lower strip 98, but could also secure upper strip 97 directly to body-contacting surface 11. Prior to use, adhesive tab 96, upper adhesive strip 97, and lower adhesive strip 98 will all be protected by removable non-adhesive liners (not illustrated).

Figure 13:
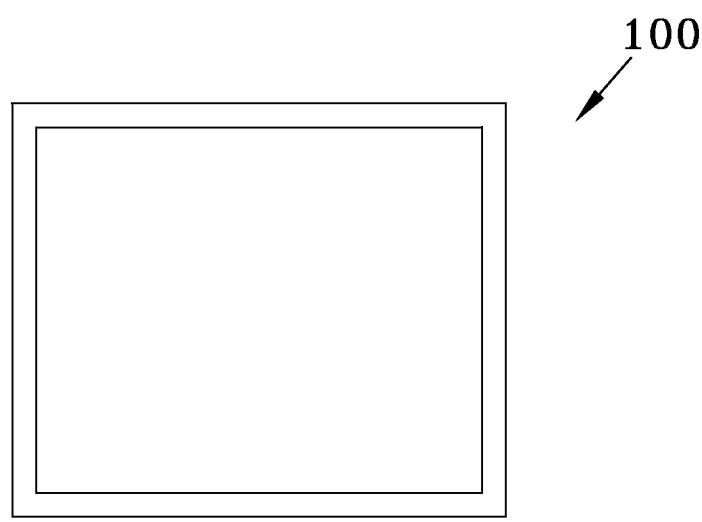
FIG. 13 is a top view of the airtight inner package embodying principles of the invention.

To contain all embodiments disclosed herein, package 100 is illustrated in FIG. 13. In order to prevent contamination, package 100 is seam sealed, and hence air and fluid tight. Although not illustrated, package 100 may be housed in a resealable package to store any unused portion of the pad for later sue, or for disposal of a used pad. Additionally, while not illustrated, all pads disclosed herein may be connected together in a sheet or roll and separated for use as needed via perforated seam.

It is important to note the embodiments discussed herein and illustrated in FIGS. 1-12 are not exhaustive in scope, and it would be obvious to those skilled in the art that reagent test tab areas could be added to any region of a sanitary/incontinence pad, or that one or more micro-perforated seam(s) flanked by two seam seals could reside therethough any section of sanitary/incontinence pad regardless of the shape, length, width, or thickness of the sanitary/incontinence pad without departing from the scope of the present invention.

The invention claimed is:

1. A pad comprising:
a body-contacting surface opposite a clothing surface, wherein an absorbent core separates said body-contacting surface from said clothing surface;
wherein a hydrophobic backsheet resides on said clothing surface of said pad;
a micro-perforated seam extending through said pad along the lateral centerline wherein said micro-perforated seam is flanked on each side by a seam seal of said micro-perforated seam, allowing said pad to be separated along said micro-perforated seam into two functioning pads;
a reagent test tab area located on said body-contacting surface comprising a non-reactive substrate with one or more reagent test tabs secured to the non-reactive substrate via an adhesive and said non-reactive substrate is secured to said absorbent core via an adhesive, wherein a reagent test tab area is located on each side of said micro-perforated seam;
an absorbent area surrounding said absorbent core;
wherein two wings are adjacent to and extend laterally from said longitudinal edges of said absorbent area and are configured to fold over the edges of an user's underwear;
said backsheet extends on said wings and further comprise two parallel rectangular regions of pressure sensitive adhesive;
said pressure sensitive adhesive is covered with a removable wing-release liner, which secures said wings together; and
said micro-perforated seam extends through said parallel rectangular regions of pressure sensitive adhesive and said removable wing-release liner.

\* \* \* \* \*